US009220465B2

(12) United States Patent
Takamura (10) Patent No.: US 9,220,465 B2
(45) Date of Patent: Dec. 29, 2015

(54) RADIOGRAPHIC APPARATUS (75) Inventor: Shoji Takamura, Kidzugawa (JP)

(73) Assignee: SHIMADZU CORPORATION, Kyoto (JP)

( * ) Notice: Subject to any disclaimer, the term of this patent is extended or adjusted under 35 U.S.C. 154(b) by 346 days.

(21) Appl. No.: 13/808,898

(22) PCT Filed: Jul. 6, 2011

(86) PCT No.: PCT/JP2011/003856
§ 371 (c)(1),
(2), (4) Date: Jan. 7, 2013

(87) PCT Pub. No.: WO2012/004986
PCT Pub. Date: Jan. 12, 2012

(65) Prior Publication Data
US 2013/0108018 A1 May 2, 2013

(30) Foreign Application Priority Data
Jul. 6, 2010 (JP) ................. 2010-154047

(51) Int. Cl.
*A61B 6/06* (2006.01)
*A61B 6/02* (2006.01)
*A61B 6/00* (2006.01)

(52) U.S. Cl.
CPC .............. *A61B 6/022* (2013.01); *A61B 6/4429* (2013.01); *A61B 6/4452* (2013.01); *A61B 6/487* (2013.01); *A61B 6/505* (2013.01)

(58) Field of Classification Search
CPC .... A61B 6/4429; A61B 6/4452; A61B 6/027; A61B 6/032; A61B 6/06; A61B 6/4291; A61B 6/54; G01N 23/046

USPC ............. 378/189, 181, 193, 147, 110, 42, 62, 378/19, 21, 4, 8, 102, 196, 198; 250/363.03, 370.09, 505.1, 515.1
See application file for complete search history.

(56) References Cited

U.S. PATENT DOCUMENTS 7,306,368 B2 * 12/2007 Isono et al. .................... 378/189
7,613,275 B2 * 11/2009 Li et al. ............................ 378/8
(Continued)

FOREIGN PATENT DOCUMENTS

EP 1484017 A1 12/2004
JP 2004358255 A 12/2004
(Continued)

OTHER PUBLICATIONS

Chinese Office Action issued in Chiense Application No. 201180033522.6 dated Jun. 30, 2014.

*Primary Examiner* — David A Vanore
(74) *Attorney, Agent, or Firm* — McDermott Will & Emery LLP (57) ABSTRACT Provided is a radiographic apparatus that can conduct radiography for an appropriate imaging region although a subject bends in a body-side direction. With one example of this invention, two or more fluoroscopic X-ray images successively taken are connected to generate a single fluoroscopic X-ray image. With a conventional configuration, when a subject bending in the body-side direction is imaged, the subject extends off a detecting surface of an FPD in the body-side direction. As a result, it is difficult to take an entire image of the subject. Thus, with the example, a detecting surface 4a is moved along a path F inclined relative to a vertical direction to successively take fluoroscopic X-ray images of the subject. The fluoroscopic X-ray images can be successively taken along bending curvature of the subject, which enables to take an entire image of the bending subject easily.

6 Claims, 9 Drawing Sheets

(56) References Cited

U.S. PATENT DOCUMENTS

| | | |
|---|---|---|
| 7,940,887 B2 * | 5/2011 | Shibata et al. .................. 378/21 |
| 7,978,811 B2 * | 7/2011 | Sakai .............................. 378/21 |
| 8,385,623 B2 * | 2/2013 | Sakai et al. ................... 382/132 |
| 8,406,377 B2 * | 3/2013 | Iwakiri et al. ................ 378/98.8 |
| 8,411,823 B2 * | 4/2013 | Tonami ......................... 378/154 |
| 8,581,197 B2 * | 11/2013 | Tonami et al. ........... 250/363.03 |
| 8,929,512 B2 * | 1/2015 | Kamitake .................... 378/102 |
| 2004/0005031 A1 * | 1/2004 | Akutsu et al. ................. 378/156 |
| 2004/0247081 A1 | 12/2004 | Halsmer et al. |
| 2005/0135560 A1 * | 6/2005 | Dafni et al. ................... 378/101 |
| 2007/0053499 A1 | 3/2007 | Isono |
| 2007/0237286 A1 * | 10/2007 | Imai .................................. 378/4 |
| 2008/0219567 A1 * | 9/2008 | Claus et al. ................... 382/232 |
| 2009/0272909 A1 * | 11/2009 | Takenaka et al. ........ 250/370.09 |
| 2009/0304144 A1 * | 12/2009 | Beyerlein et al. ............... 378/19 |
| 2009/0304145 A1 * | 12/2009 | Schlomka ........................ 378/19 |
| 2011/0170660 A1 * | 7/2011 | Atzinger et al. ................ 378/51 |
| 2012/0114098 A1 * | 5/2012 | Mikami et al. .................. 378/62 |
| 2012/0140886 A1 * | 6/2012 | Murakoshi et al. ............. 378/62 |

FOREIGN PATENT DOCUMENTS

| | | |
|---|---|---|
| JP | 3118190 U | 1/2006 |
| JP | 200768578 A | 3/2007 |

* cited by examiner

RADIOGRAPHIC APPARATUS

RELATED APPLICATIONS

This application is the U.S. National Phase under 35 U.S.C. §371 of International Application No. PCT/JP2011/003856, filed on Jul. 6, 2011, which in turn claims the benefit of Japanese Application No. 2010-154047, filed on Jul. 6, 2010, the disclosures of which Applications are incorporated by reference herein.

TECHNICAL FIELD

This invention relates to a radiographic apparatus for taking images through irradiating a subject with radiation. More particularly, this invention is directed to a radiographic apparatus that can conduct examinations of scoliosis.

BACKGROUND

Figure 15:
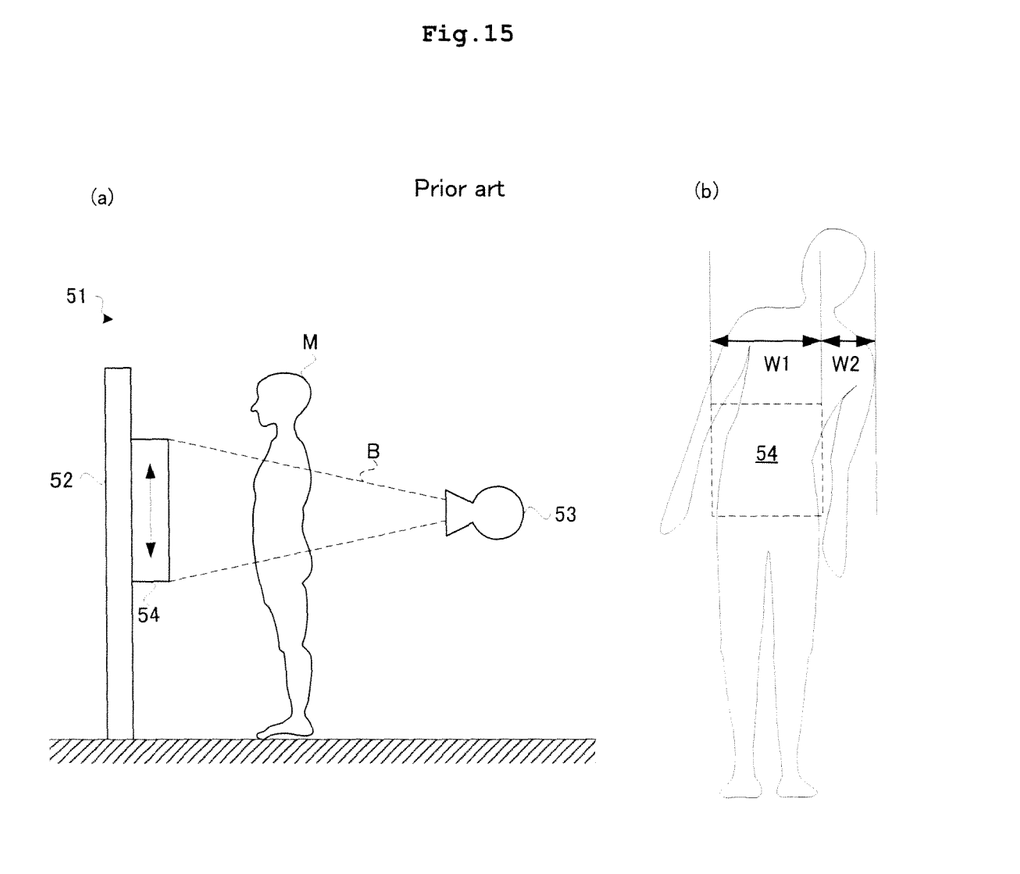
FIG. 15 is a schematic view showing a conventional X-ray apparatus.

Medical institutions have a radiographic apparatus installed therein for taking images of a subject M. As shown in FIG. 15(a), such a radiographic apparatus 51 includes a radiation source 53 and a radiation detector 54 across the subject M in a standing posture. The radiation source 53 is provided for emitting radiation in a horizontal direction along a floor of an examination room. The radiation detector 54 is provided for detecting the radiation transmitting through the subject M. See Utility Model Registration No. 3118190.

The radiation detector 54 has a square detecting surface that detects radiation. The radiation detector 54 is arranged such that the detecting surface thereof is orthogonal to a central axis of a radiation beam B from the radiation source 53 (as if the detecting surface stands). The radiation detector 54 is supported on a strut 52. The radiation detector 54 is movable in a vertical direction along the strut 52. The detecting surface generally has a size to cover a width in a body side direction of the standing subject M in an erect posture. The detecting surface of the radiation detector 54 is not limited to be square, but may be rectangular.

In actual examinations, a region of the subject M to be imaged may be larger than the detecting surface of the radiation detector 54. In such case, radiography is conducted multiple times while the radiation detector 54 is moved in the vertical direction to obtain two or more images. The obtained images are superimposed to generate one image. Such radiography method is often used for imaging a body portion of the subject M.

However, the conventional radiographic apparatus has the following drawback. That is, the conventional radiographic apparatus is not suitable for examinations of scoliosis. Scoliosis is a condition where a backbone bends in a body-side direction of the subject M. In order to diagnose scoliosis, the subject M is imaged while bending in the body-side direction as in FIG. 15(b).

When a symptom of the backbone is observed with the subject M bending as above, a region of the subject M to be imaged (an imaging region of object) becomes larger than the detecting surface of the radiation detector 54. As a result, it is necessary to connect two or more images obtained during vertical movement of the radiation detector 54 to generate a single image. The radiation detector of the conventional apparatus, however, is moved only in the vertical direction. Here, the subject M bends in the body-side direction (i.e., a horizontal direction). Accordingly, the body portion of the subject M does not extend in the vertical direction. Consequently, the body portion of the subject M extends in a direction different from a moving direction of the radiation detector 54. Consequently, the body portion of the subject M may be partially out of an imaging field of view of the radiographic apparatus 51.

Specifically, as shown in FIG. 15(b), the radiographic apparatus 51 cannot have the imaging region with a width larger than a width W1 of the radiation detector 54. Thus, radiography cannot be conducted to a width W2 of the body portion of the bending subject M out of the width W1. According to the conventional configuration, although the subject M lies within the width W2, the portion of the subject M within the width W2 cannot be imaged.

This invention has been made regarding the state of the art noted above, and its object is to provide a radiographic apparatus that can conduct radiography for an appropriate imaging region although a subject bends in a body-side direction.

SUMMARY

The above object is fulfilled, according to this invention, by a radiographic apparatus including a radiation source for emitting radiation; a radiation detecting device having a detecting surface for detecting the radiation; a strut extending in a vertical direction for supporting the radiation detecting device; (A1) a strut moving device for moving the strut in a horizontal direction that is orthogonal to a direction from the radiation source toward the radiation detecting device; (B1) a strut-movement control device for controlling the strut moving device; a detector vertically-moving device for moving the radiation detecting device vertically relative to the strut; a detector vertical-movement control device for controlling the detector vertically-moving device; an image generating device for generating images based on detection data outputted from the radiation detecting device; and a connecting device for connecting two or more images successively taken to generate a single image. The detecting surface is placed along a plane formed by the vertical and horizontal directions. The strut moving device and the detector vertically-moving device move the radiation detecting device along a path inclined relative to the vertical direction upon taking the images successively.

Operation and Effect

According to an aspect of this invention, two or more images successively taken are connected to one another generate a single image. Consequently, although the imaging region does not fall within the detecting surface of the radiation detecting device entirely by once radiography, fluoroscopic images of the subject can be obtained. On the other hand, with the conventional configuration, when the subject bending in the body-side direction is imaged for examinations of scoliosis, the subject extends off the detecting surface of the radiation detecting device in the body-side direction. As a result, it is difficult to take the entire image of the subject. Thus, according to one aspect of this invention, the detecting surface is moved along the path inclined relative to the vertical direction to successively take fluoroscopic images of the subject. Then the fluoroscopic images can be successively taken along the bending subject, which enables to take the entire image of the bending subject more easily.

The radiographic apparatus according to the aspect of this invention may include, instead of (A1) the strut moving device for moving the strut in the horizontal direction that is orthogonal to the direction from the radiation source toward the radiation detecting device, (A2) a detector horizontally-moving device for moving the radiation detecting device relative to the strut in a horizontal direction that is orthogonal to a direction from the radiation source toward the radiation detecting device. With the modification of the aspect, (B1) the strut-movement control device for controlling the strut moving device is replaced with (B2) a detector horizontal-movement control device for controlling the detector horizontally-moving device. In other words, the radiation detecting device may be moved in the horizontal direction through horizontal movement of the strut for supporting the radiation detecting device or horizontal movement of the radiation detecting device relative to the strut.

The radiographic apparatus mentioned above further includes an input unit for inputting instructions by an operator. The path where the detecting surface is moved during successive imaging is set by the operator through identifying two vertices on a diagonal of the rectangular imaging region. Such configuration is more desirable.

Operation and Effect

The above configuration represents one aspect of this invention. Specifically, the path where the detecting surface is moved during successive imaging is set by the operator through identifying two vertices on the diagonal of the rectangular imaging region. Accordingly, the detecting surface of the radiation detecting device is moved as the way the operator instructs. Therefore, a radiographic apparatus that enables to conduct examinations easily can be provided.

The radiographic apparatus mentioned above further includes a collimator for collimating the radiation emitted from the radiation source into a cone-shaped radiation beam. The cone-shaped radiation beam in a plane where the detecting surface of the radiation detecting device lies has a horizontal width corresponding to a sum of a horizontal width of the detecting surface and a moving width by which the detecting surface is moved in the horizontal direction during successive imaging. Such configuration is more desirable.

Operation and Effect

The above configuration represents one aspect of this invention. Specifically, the horizontal width of the cone-shaped radiation beam in the plane where the detecting surface of the radiation detecting device lies corresponds to the sum of the horizontal width of the detecting surface and the moving width by which the detecting surface is moved in the horizontal direction during successive imaging. That is, the horizontal width of the radiation beam reliably covers the movable detecting surface entirely. Such configuration can achieve successive imaging for fluoroscopic images without moving the radiation source horizontally. In other words, successive imaging is conducted while a focus of the radiation source for emitting radiation is not moved. Consequently, images of the subject appearing in each fluoroscopic image are taken with a common irradiation focus. Each fluoroscopic image is taken with common distortion. When they are connected to one another, no difference in level occurs in connecting portions, which can achieve ideal connection of the images.

The radiographic apparatus mentioned above further includes a radiation-source moving device for moving the radiation source in the horizontal direction viewed from the radiation detecting device; and a radiation-source movement control device for controlling the radiation-source moving device. The radiation source is moved horizontally along with horizontal movement of the strut such that a relative relationship in the horizontal direction between the radiation source and the radiation detecting device is constant, whereby the images are successively taken. Such configuration is more desirable.

Operation and Effect

The configuration mentioned above represents one aspect of taking images successively while the focus of the radiation source for emitting radiation is moved horizontally. Such configuration can achieve a constant relative relationship in the horizontal direction between the radiation source and the radiation detecting device. Accordingly, a central axis of the radiation beam can be located at the center of the detecting surface of the radiation detecting device in every radiography. Consequently, fluoroscopic images having the center with less distortion can be obtained.

The radiographic apparatus mentioned above further includes a collimator for collimating the radiation emitted from the radiation source into a cone-shaped radiation beam. The cone-shaped radiation beam in a plane where the detecting surface of the radiation detecting device lies has a horizontal width corresponding to a horizontal width of the detecting surface. Such configuration is more desirable.

Operation and Effect

The configuration mentioned above represents one aspect of taking images successively while the focus of the radiation source for emitting radiation is moved horizontally. When the horizontal width of the cone-shaped beam in the plane where the detecting surface of the radiation detecting device lies corresponds to the horizontal width of the detecting surface, the radiation beam can be applied to the subject without extending off the detecting surface in the horizontal direction. Consequently, the radiographic apparatus can be provided that can minimize an exposure to the subject.

According to the aspect of this invention, two or more images successively taken are connected to one another to generate a single image. On the other hand, with the conventional configuration, when the subject bending in the body-side direction is imaged for examinations of scoliosis, the subject extends off the detecting surface of the radiation detecting device in the body-side direction. As a result, it is difficult to take the entire image of the subject. Thus, according to the aspects of this invention, the detecting surface is moved along the path inclined relative to the vertical direction to successively take fluoroscopic images of the subject. Then the fluoroscopic images can be successively taken along the bending subject, which enables to take the entire image of the bending subject easily.

DETAILED DESCRIPTION

Now, description will be given of the best mode for carrying out this invention.

EXAMPLE 1

Examples of this invention will be described hereinafter. X-rays in the examples correspond to the radiation in this invention. An FPD is the abbreviation of a flat panel detector.

<Whole Configuration of X-ray Apparatus>

Figure 1:
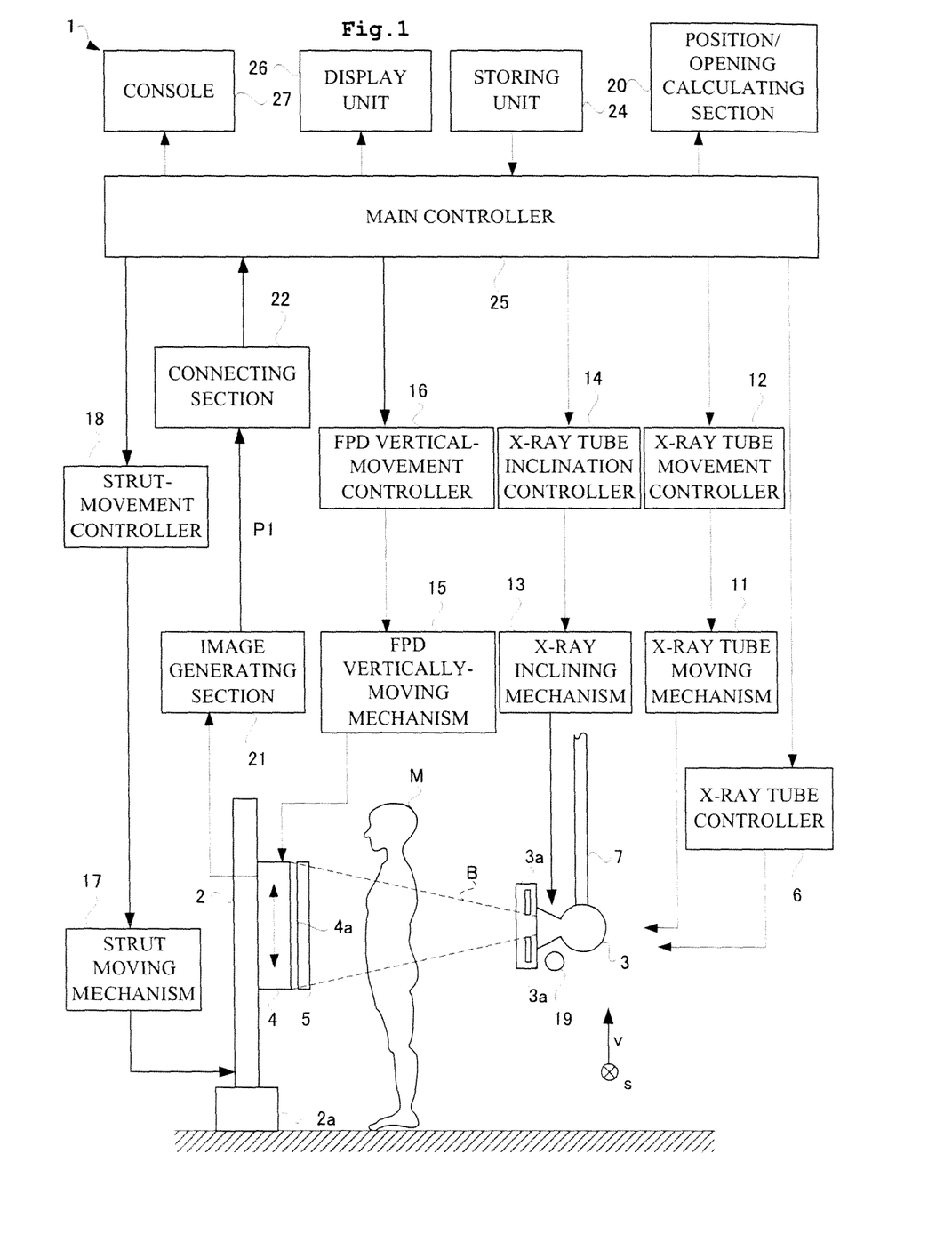
FIG. 1 is a functional block diagram showing a configuration of an X-ray apparatus according to one example of this invention.

Firstly, description will be given of an X-ray apparatus 1 according to Example 1. The X-ray apparatus 1 conducts radiography to a subject M in a standing posture. As shown in FIG. 1, the X-ray apparatus 1 includes a strut 2 extending from a floor in a vertical direction v; an X-ray tube 3 for emitting X-rays; an FPD 4 supported by the strut 2; and a suspension-support member 7 extending in the vertical direction v and supported on the ceiling. The suspension-support member 7 suspends and supports an X-ray tube 3.

The FPD 4 can slide in the vertical direction v relative to the strut 2. The suspension-support member 7 expands and contracts in the vertical direction v. As the suspension-support member 7 expands and contracts, a position of the X-ray tube 3 in the vertical direction v changes. The FPD 4 is moved in the vertical direction v relative to the strut 2 by an FPD vertically-moving mechanism 15 provided between the elements 2 and 4. The FPD vertically-moving mechanism 15 is controlled by an FPD vertical-movement controller 16.

Description will be given of movement of the strut 2. The strut 2 is movably placed on a rail 2a. The rail 2a is fixed on a floor of an examination room and extends in a direction from the X-ray tube 3 toward the FPD 4. A strut moving mechanism 17 moves the strut 2 in a horizontal direction s that is orthogonal to the direction from the X-ray tube 3 toward the FPD 4. A strut-movement controller 18 is provided for controlling this movement.

Description will be given of movement of the X-ray tube 3. The X-ray tube 3 is moved by an X-ray tube moving mechanism 11 provided in the suspension support member 7. An X-ray tube movement controller 12 controls the X-ray tube moving mechanism 11. The X-ray tube 3 is moved by the X-ray tube moving mechanism 11 in (1) the vertical direction v, (2) an approaching and moving-away direction relative to the FPD 4, and (3) the horizontal direction s (i.e., a direction passing through the plane of FIG. 1, a body-side direction of the subject M) that is orthogonal to the direction from the X-ray tube 3 toward the FPD 4. When the X-ray tube 3 is moved in the vertical direction v, the suspension-support member 7 expands and contracts.

The FPD 4 has a detecting surface 4a (see FIG. 1) for detecting X-rays. The X-ray apparatus 1 includes the detecting surface 4a erecting in the vertical direction v. Thereby, the erecting subject M can be imaged efficiently. The detecting surface 4a is placed so as to face to an X-ray irradiation hole of the X-ray tube 3. In other words, the detecting surface 4a is placed along a plane formed by two directions, i.e., the horizontal direction s and the vertical direction v. The detecting surface 4a is rectangular, and one side thereof conforms to the horizontal direction s, whereas the other one side orthogonal to the side conforms to the vertical direction v.

An X-ray grid 5 is provided so as to cover the detecting surface 4a of the FPD 4. The X-ray grid 5 has vertically-elongated strips of absorption foil arranged in the horizontal direction s. X-rays scattering within the subject M and having wrong directions enter into the strips of absorption foil, and thus fail to reach the FPD 5. Such configuration can eliminate the influence of the scattered X-rays obstructive of obtaining profile views of the subject M, which results in clear fluoroscopic X-ray images.

An X-ray tube controller 6 is provided for controlling the X-ray tube 3 with a tube voltage, a tube current, a pulse width, and an irradiation time of X-rays. An X-ray tube controller 6 controls the X-ray tube 3 so as to output radiation with a given tube current, a tube voltage, and a pulse width. Parameters such as the tube current are stored in a storing unit 24.

Description will be given of a collimator 3a provided in the X-ray apparatus 1. The collimator 3a is attached to the X-ray tube 3 for collimating X-rays emitted from the X-ray tube 3 to generate an X-ray beam B in a quadrangular pyramid (cone) shape.

Figure 2:
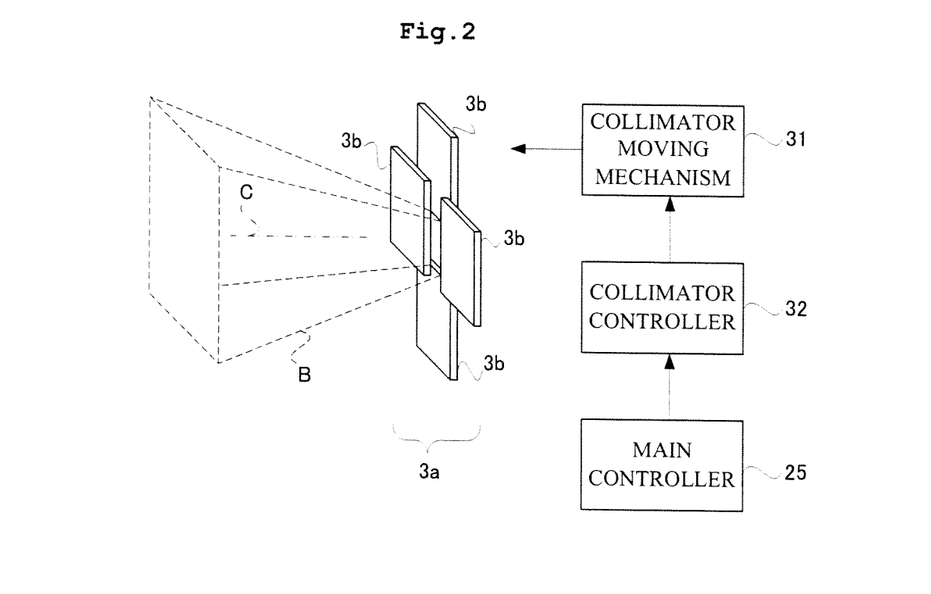
FIG. 2 is a perspective view showing a collimator according to the example of this invention.

The collimator 3a is to be described in detail. As shown in FIG. 2, the collimator 3a has one pair of leaves 3b that moves in a mirror-image symmetrical manner relative to a center axis C, and has one more pair of leaves 3b that similarly moves in a mirror-image symmetrical manner relative to the center axis C. Movement of the leaves 3b of the collimator 3a can achieve not only irradiation of an entire detecting surface 4a of the FPD 4 with an X-ray beam B in a cone shape, but also irradiation of only a center portion of the FPD 4 with an X-ray beam B in a fan shape. Here, the center axis C also represents the center of the X-ray beam B. One pair of the leaves 3b controls divergence of the quadrangular pyramid X-ray beam in the vertical direction v. The other pair of the leaves 3b controls divergence of the X-ray beam in the horizontal direction s. A collimator moving mechanism 31 changes opening of the collimator 3a. A collimator controller 32 controls the collimator moving mechanism 31.

Moreover, instead of the configuration in which the collimator 3a is moved in a mirror-image symmetrical manner, a configuration in which one pair of leaves 3b moves independently may be adopted. In such independent control type collimator 3a, merely movement of the leaves 3b of the collimator 3a independently without moving the X-ray focus in the vertical and horizontal directions can achieve free change in irradiation position of the X-ray beam. In this case, the focus of the X-ray tube 3 is not moved, but the irradiation position of the X-ray beam is changed while inclination of the X-ray tube 3 is changed by an X-ray inclining mechanism 13, to be mentioned later.

Figure 3:
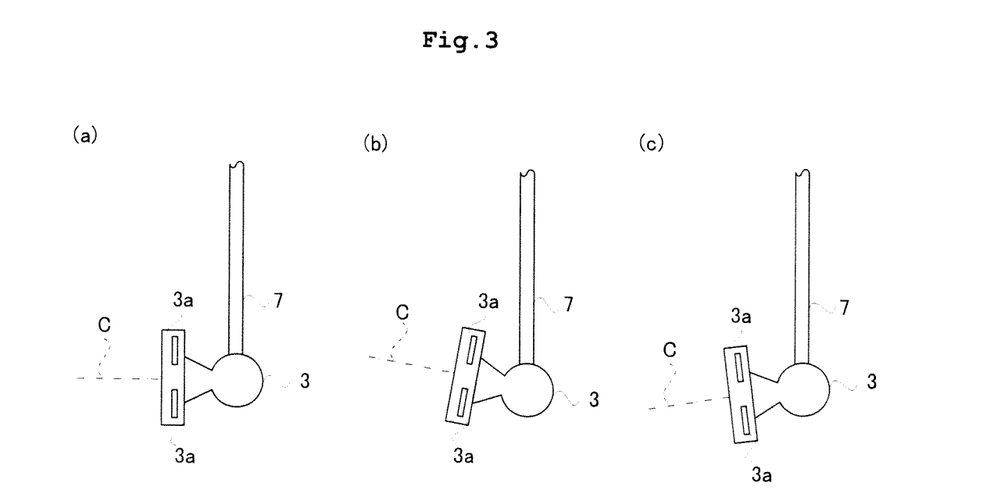
FIG. 3 is a schematic view showing inclination of an X-ray tube according to the example of this invention.

Description will be given of inclination of the X-ray tube 3. The X-ray tube 3 can be inclined from a state where the central axis C of the X-ray beam B is parallel to the floor of the examination room (see FIG. 3(*a*)) into a state where the central axis C may be inclined upward toward the vertical direction (see FIG. 3(*b*)), or into a state where the central axis C may be inclined downward toward the vertical direction (see FIG. 3(*c*)). Such inclination of the X-ray tube 3 is performed by the X-ray tube inclining mechanism 13. An X-ray tube inclination controller 14 is provided for controlling this inclination.

A visible light source 19 is attached to the X-ray tube 3 (see FIG. 1). Visible light emitted from the visible light source 19 is collimated with the collimator 3*a*, and then travels toward a detecting surface 4*a* side of the FPD 4. In examinations, the subject M is placed between the X-ray tube 3 and the FPD 4. Visible light is firstly emitted from the visible light source 19, and then X-rays are emitted from the X-ray tube 3 without moving the leaves 3*b* of the collimator 3*a*. Here, a portion of the subject M irradiated by the visible light source 19 conforms to an incident portion of the subject M to which X-rays are applied from the X-ray tube 3. As above, visible light is applied to the subject M prior to X-ray irradiation, whereby the portion of the subject M to which X-rays are to be applied can be identified.

A position/opening calculating section 20 calculates opening of the collimator 3*a*, a position of the X-ray tube 3, an inclination angle of the X-ray tube 3, and a position of the FPD 4 such that a region of the subject M set in advance through irradiation of visible light can be imaged. Each controller 12, 14, 16, and 18 controls each mechanism using calculation results of the position/opening calculating section 20.

An image generating section 21 constructs detection data outputted from the FPD 4, and generates a fluoroscopic X-ray image having a profile view of the subject M appearing therein. A connecting section 22 connects two or more fluoroscopic X-ray images having various positions of the subject M appearing therein, thereby producing a single image. For instance, supposing that three fluoroscopic X-ray images having a chest, an abdomen, and a waist of the subject M each appearing therein are successively taken, the connecting section 22 connects these three fluoroscopic X-ray images to generate a single long image. The connected fluoroscopic X-ray image is displayed on a display screen 26.

A console 27 is provided for inputting each instruction from an operator. A storing unit 24 stores all parameters used for X-ray radiography, such as control information of the X-ray tube 3, positional information of the X-ray tube 3, opening of the collimator 3*a*, inclination information of the X-ray tube 3, positional information of the FPD 4 in the vertical direction v, and positional information of the strut in the horizontal direction s. As shown in FIG. 1, the X-ray apparatus 1 also includes a main controller 25 for controlling en bloc each section 6, 12, 14, 16, 18, 20, 21, 22, 24. The main controller 25 has a CPU, and provides the above components by executing various programs. The above components may be divided into arithmetic units that perform their functions.

<Operation of X-ray Apparatus>

Figure 4:
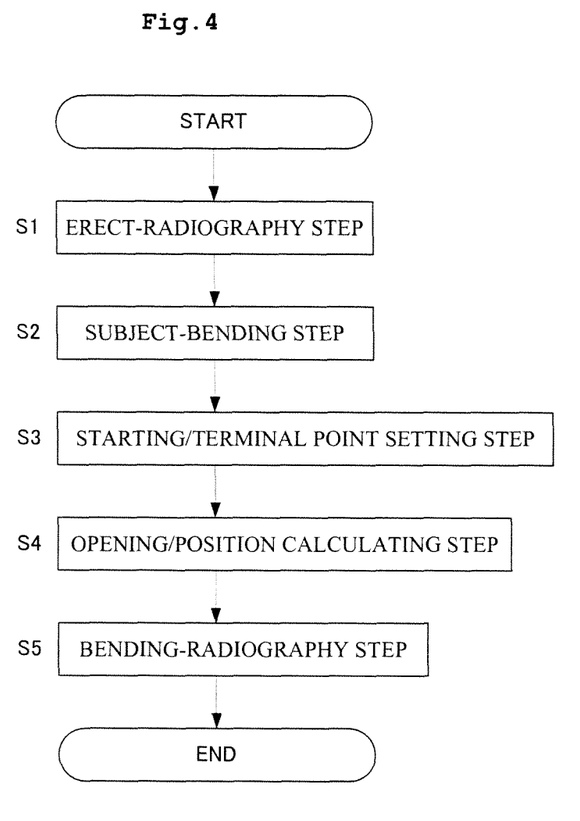
FIG. 4 is a flow chart showing operations of the X-ray apparatus according to the example of this invention.

Next, description will be given of operations of the X-ray apparatus 1. Specifically, description will be given of an examination of scoliosis as one example for expressing the feature of this invention most effectively. For conducting the examination of scoliosis, the subject M is imaged under a standing state, and then the subject M is imaged while bending in the horizontal direction s. More specifically, as shown in FIG. 4, a fluoroscopic X-ray image of the subject M is obtained while the subject M is placed in an erect state between the X-ray tube 3 and the FPD 4 (an erect-radiography step S1.) Thereafter, an instruction is provided to the subject M so as to bend (a subject-bending step S2), and then a starting point and a terminal point are set so as to identify an imaging region (a starting/terminal point setting step S3.) Thereafter, opening of the collimator 3*a* and positions of each section 2, 3, 4, is calculated upon radiography (an opening/position calculating step S4), and actual bending radiography is started in accordance with the calculated positions (a bending-radiography step S5.) Each of these steps will be described hereinafter in order.

<Erect-Radiography Step S1>

Firstly, the subject M is placed as to erect between the X-ray tube 3 and the FPD 4. In the erect-radiography, it is necessary to image the back bone of the subject M. Thus, the detecting surface 4*a* of the FPD 4 fails to cover the imaging region. Accordingly, actual X-ray radiography is conducted three times for upper, center, and lower sides of the subject M.

Figure 5:
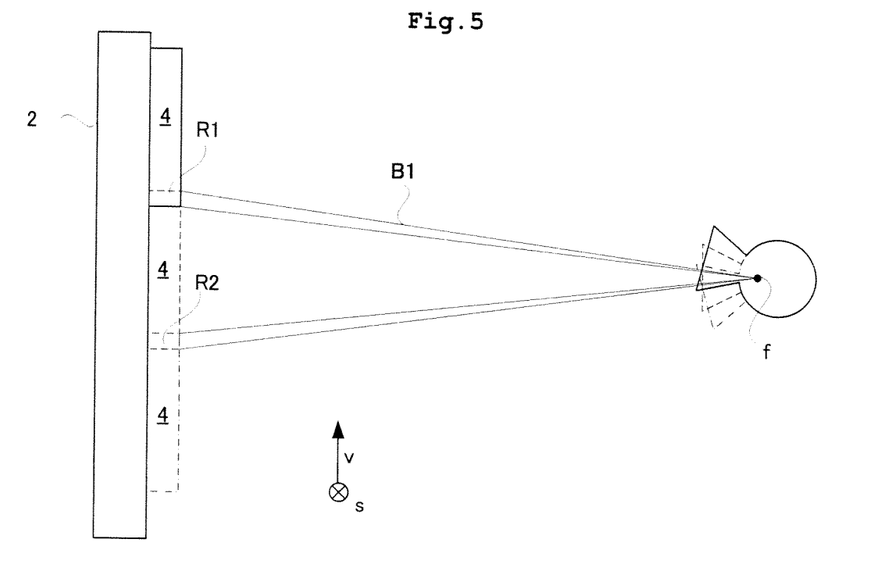
FIG. 5 is a schematic view showing movement of an FPD for standing radiography according to the example of this invention.

When the operator provides an instruction via the console 27 to start radiography, the FPD 4 is moved upward as shown in FIG. 5, and then is stopped at a position shown by solid lines in FIG. 5. Simultaneously, the X-ray tube 3 is inclined upward and is stopped at a position shown by solid lines. X-ray radiography is conducted under this state, whereby a fluoroscopic X-ray image for the chest of the subject M can be obtained. Then the FPD 4 is moved vertically downward and is stopped at a position shown by dotted lines in FIG. 5. Simultaneously, the X-ray tube 3 is inclined downward and is stopped at a position shown by dotted lines. X-ray radiography is again conducted under this state, whereby a fluoroscopic X-ray image for the abdomen of the subject M can be obtained.

Thereafter, the FPD 4 is moved vertically downward, and is stopped at a position shown by dashed lines in FIG. 5. Simultaneously, the X-ray tube 3 is inclined downward, and is stopped at a position shown by dashed lines. Radiography is conducted under this state, whereby a fluoroscopic X-ray image for the waist of the subject M can be obtained.

Three obtained fluoroscopic X-ray images are sent to the connecting section 22, where a single long image having the back bone appearing therein can be obtained. The detailed configuration of the connected section 22 is to be mentioned later.

Description will be given of a reason for inclination of the X-ray tube 3. As the X-ray tube 3 is inclined, the X-ray tube 3 rotates. Here note that a rotation center thereof corresponds to a focus f of the X-ray tube 3 for X-ray irradiation. When radiography is conducted to the elongated image for several times, conforming focuses for X-ray irradiation can achieve ideal connection of the fluoroscopic X-ray images.

It is essential for the configuration of the example to connect the fluoroscopic X-ray images satisfactorily by inclination of the X-ray tube 3. Here, description will be given of a relationship between an imaging method having the same focus f and connection of the fluoroscopic X-ray images. For instance, a region R1 in FIG. 5 is so-called an overlap width of a connecting portion of the images taken at both first and second radiography. The X-ray beam denoted by B1 in FIG. 5 enters into the FPD 4 to image the region R1 at every radiography. That is because X-rays from the common focus f reach the region R1 in every radiography, and thus the region R1 is imaged.

Since the X-ray beam diverges radially about the focus f, the image obtained by projecting the beam on the subject M is distorted. Specifically, as X-rays enter into the subject M obliquely, distortion becomes remarkable. As shown in FIG. 5, radiography is conducted to the region R1 with the common focus f for all of the first and second fluoroscopic X-ray images. Consequently, both fluoroscopic X-ray images have the region R1 with same distortion. Thus, when both fluoroscopic X-ray images are connected, they can be combined naturally with no step at the connecting portion.

Such relationship is same as that of a region R2 as an overlap portion at second and third radiography. That is because X-rays from the common focus f in every radiography reach the region R2, and thus the region R2 is imaged.

<Subject Bending Step S2, Starting Point/Terminal Point Setting Step S3>

Figure 6:
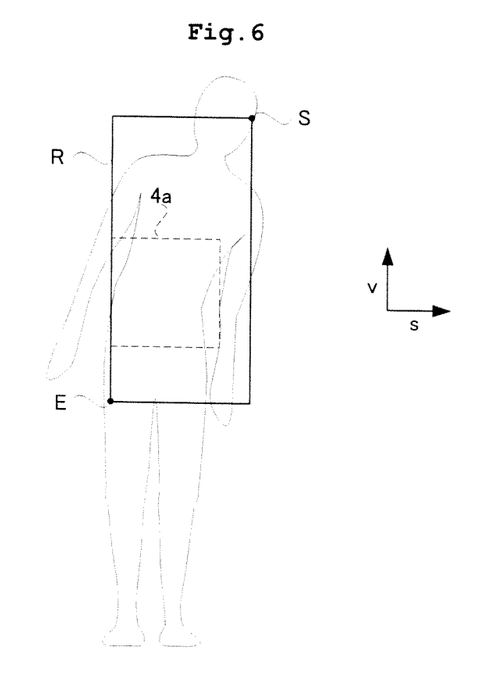
FIGS. 6 and 7 are schematic views each showing a method of identifying a starting point and a terminal point prior to bending radiography according to the example of this invention.

Next, as shown in FIG. 6, the operator provides an instruction to bend the subject M in the body axis direction (a subject bending step S2.) Then the operator switches the visible light source 19 on via the console 27, whereby visible light is applied to the bending subject M. The visible light is collimated by the collimator 3a for determining a width of the X-ray beam. As a result, the operator can recognize the irradiation region of X-rays through observing a portion of the subject M where visible light is applied.

Thereafter, the operator determines an imaging region of object R shown in FIG. 6. The imaging region of object R expresses an X-ray irradiation region when X-ray radiography is conducted to the bending subject. The width of the subject M in the horizontal direction s in the imaging region of object R is larger than a width of the detecting surface 4a of the FPD 4 shown by dotted lines in FIG. 6. Likewise, a width of the subject M in the body axis direction in the imaging region of object R is larger than that of the detecting surface 4a.

The operator identifies a starting point S and a terminal point E, whereby the X-ray apparatus 1 recognize a position of the imaging region of object R. The starting point S and the terminal point E correspond to two vertices on a diagonal of the rectangular imaging region of object R. Thus, in Example 1, it is supposed that the starting point S is located vertically upward from the terminal point E. When the starting point S and the terminal point E are identified, a path where the detecting surface 4a is moved during three-time X-ray radiography is set. Accordingly, the moving range of the FPD 4 in the vertical direction v and that of the strut in the horizontal direction s are determined.

Figure 7:
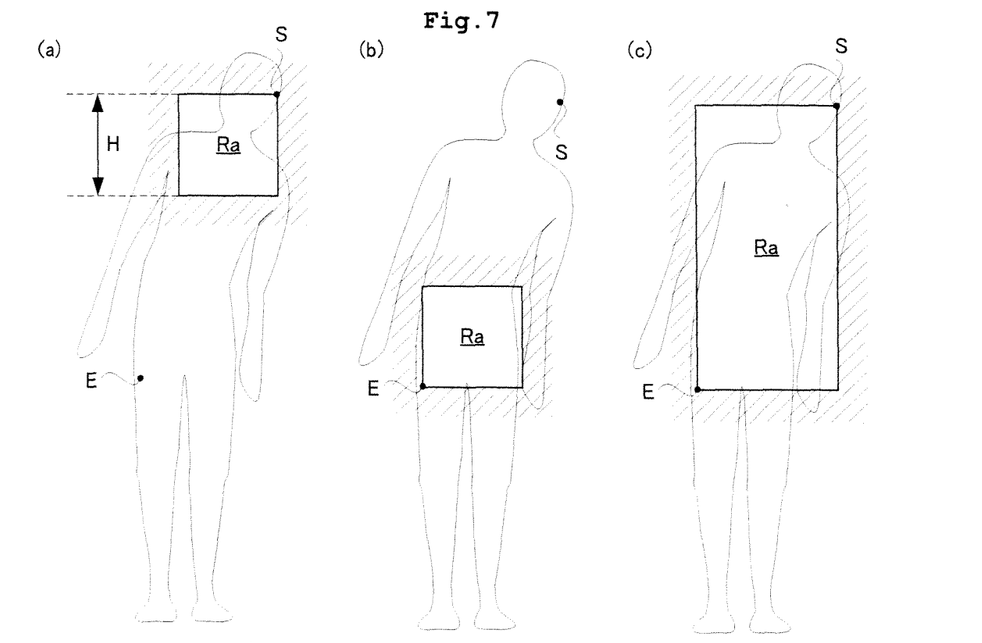

Detailed description will be given of a method of setting the starting point S and the terminal point E. The operator moves the X-ray tube 3 in the vertical direction v, the horizontal direction s, and the body axis direction while applying visible light to the subject M, and determines a position of the X-ray tube 3 for X-ray radiography. Thereafter the operator adjusts the collimator 3a. Consequently, as shown in FIG. 7(a), a region Ra where visible light is applied to the subject M is adjusted such that one vertex of the region Ra conforms to the starting point S of the imaging region of object R. Here, it is preferable that a height H of the region Ra conforms to a level of the FPD 4 in the vertical direction v. More strictly, visible light diverges radially. Accordingly, when visible light transmits through the subject M into the detecting surface 4a of the FPD 4, it is more preferable that visible light is set so as not to be applied out of the detecting surface 4a in the vertical direction v. The operator operates the console 27 when one vertex of the region Ra conforms to the starting point S, and the X-ray apparatus 1 registers the starting point S.

Thereafter, the X-ray tube 3 inclines without varying its position. Thereby the region Ra is moved downward to the left. Then, as shown in FIG. 7(b), the region Ra where visible light is applied to the subject M is adjusted such that one vertex thereof conforms to the terminal point E of the imaging region of object R. The operator operates the console 27 when one vertex of the region Ra conforms to the terminal point E, and the X-ray apparatus 1 registers the terminal point E. The opening of the collimator 3a, and the inclination angle and the focus position of the X-ray tube 2 when the starting point S and the terminal point E are registered are sent out from the collimator controller 16, the X-ray tube inclination controller 14, and the X-ray tube movement controller 12, respectively, and are stored into the storing unit 24. As a result, the starting point/terminal point setting step S3 is completed.

As another aspect of the starting point/terminal point setting step S3, the X-ray tube 3 sufficiently moves away from the subject M, whereby the starting point S and the terminal point E can be registered at one time (see FIG. 7(c)). Such configuration may be adopted. In this case, the imaging region of object R where X-rays are applied conforms to the region Ra where visible light is applied. Subsequent to the starting point/terminal point setting step S3, the X-ray tube 3 approaches the FPD 4 for conducting actual X-ray radiography.

<Opening/Position Calculating Step S4>

As shown in FIG. 7(c), when the X-ray tube 3 upon determining the X-ray irradiation region with visible light differs in position from the X-ray tube 3 upon X-ray irradiation, the opening of the collimator 3a and the inclination angle of the X-ray tube 3 during X-ray radiography are different from each other. Then, prior to X-ray radiography, it is necessary to determine such geometric imaging conditions in advance. In the X-ray apparatus 1 according to Example 1, the position and the inclination angle of the X-ray tube 3, and the opening of the collimator 3a are calculated by the position/opening calculating section 20. Since the imaging region of object R is larger than the FPD 4, it cannot be imaged at one time. Accordingly, actual X-ray radiography is conducted three times for upper, center, and lower sides of the imaging region of object R. The position/opening calculating section 20 performs geometric calculation for three-time radiography.

Upon registration of the starting point S and the terminal point E, the focus position for X-ray irradiation of the X-ray tube 3, the opening of the collimator 3a, and the inclination angle of the X-ray tube 3 are sent out to the position/opening calculating section 20. The position/opening calculating section 20 determines the position of the starting point S and the terminal point E relative to the focus of X-ray irradiation from the opening of the collimator 3a and the inclination angle of the X-ray tube 3 by geometric calculation.

When the focus is moved to a position where X-rays are applied, the position/opening calculating section 20 determines the opening of the collimator 3a and the inclination angle of the X-ray tube 3 suitable for X-ray irradiation to the upper portion of the imaging region of object R containing the starting point S. The position of the focus upon X-ray irradiation used for calculation by the position/opening calculating section 20 may be used as a value set in advance and read out from the storing unit 24, or may be identified by the operator.

Thereafter when the focus is moved to the position where X-rays are applied, the position/opening calculating section 20 determines the opening of the collimator 3a and the inclination angle of the X-ray tube 3 suitable for X-ray irradiation to the center portion in the vertical direction of the imaging region of object R. Then, when the focus is moved to the position where X-rays are applied, the position/opening calculating section 20 determines the opening of the collimator 3a and the inclination angle of the X-ray tube 3 suitable for X-ray irradiation to the lower portion in the vertical direction of the imaging region of object R containing the terminal point E. The opening/position calculating section 20 may determine the inclination angle before the opening, or vice versa.

When the starting point S and the terminal point E are registered as in FIGS. 7(a) and 7(b), the upper and lower of the imaging region of object R may be imaged using the same geometric conditions as those upon determination of the starting point S and the terminal point E. Accordingly, in this case, the position/opening calculating section 20 just calculates a geometric conditions for radiography in which the center portion in the vertical direction of the imaging region of object R is irradiated with X-rays.

In this way, the position/opening calculating section 20 calculates the opening and the inclination angles for three-time radiography. Each parameter obtained is stored in the storing unit 24. The position/opening calculating section 20 calculates not only the imaging conditions with respect to the position of the X-ray tube 3 but also the positions of the strut 2 for three-time radiography. The calculation for the positions of the strut 2 is to be mentioned later.

In any case, a moving range of the strut 2 is determined by the distance in the horizontal direction s between the starting point S and the terminal point E, and the width in the horizontal direction s of the FPD 4. Moreover, a moving range of the FPD 4 is determined by the distance in the vertical direction v of the starting point S and the terminal point E, and the level in the vertical direction v of the FPD 4.

<Bending-Radiography Step S5>

Figure 8:
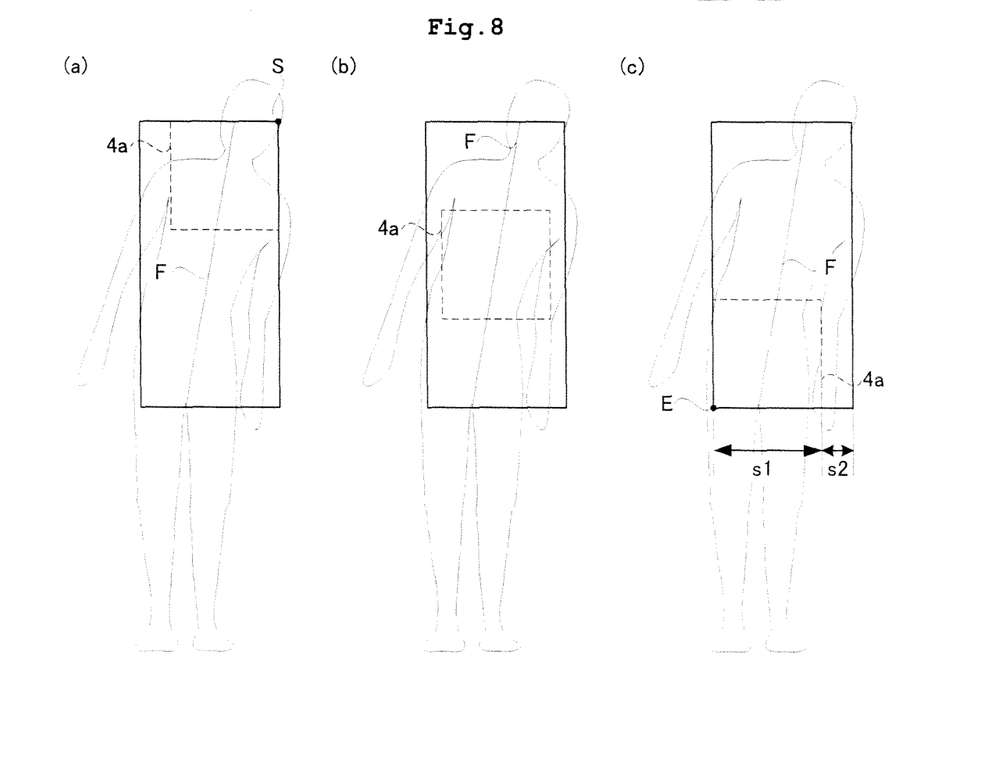
FIG. 8 is a schematic view showing movement of the FPD for bending radiography according to the example of this invention.

When the operator provides an instruction via the console 27 to the X-ray apparatus 1 to image the bending subject M, the X-ray apparatus 1 reads out the position and the inclination angle of the X-ray tube 3 and the opening of the collimator 3a stored in the storing unit 24, and then performs X-ray radiography three times. Each radiography is performed while the FPD 4 is moved in the vertical direction and the horizontal direction s. Specifically, FIG. 8(a) shows a position of the detecting surface 4a upon the first X-ray radiography. Here, one vertex of the detecting surface 4a conforms to the starting point S, and the entire of the detecting surface 4a is contained in the imaging region of object R. FIG. 8(b) shows a position of the detecting surface 4a upon the second X-ray radiography. Here, the detecting surface 4a is located at the center of the imaging region of object R in the vertical direction v and the horizontal direction s. FIG. 8(c) shows a position of the detecting surface 4a upon the third X-ray radiography. Here, one vertex of the detecting surface 4a conforms to the terminal point E, and the entire of the detecting surface 4a is contained in the imaging region of object R. The positions of the detecting surface 4a in the first and the second radiography partially overlap to each other in the vertical direction v, whereas those in the second and third radiography partially overlap in the vertical direction v.

Such movement of the FPD 4 is achieved by movement of the strut 2 in the horizontal direction s. The position/opening calculating section 20 calculates the positions of the FPD 4 for three-rime radiography from the positions of the starting point S and the terminal point E in the previous step. The calculated positions are stored in the storing unit 24. The strut movement controller 18 moves the strut 2 in the horizontal direction s such that the detecting surface 4a lies at the position shown in FIG. 8 for every radiography. In this way, the X-ray apparatus 1 in Example 1 moves the strut 2 in the horizontal direction s and the FPD 4 in the vertical direction v, thereby successively taking fluoroscopic X-ray images through moving the detecting surface 4a of the FPD 4 along a path F (FIG. 8) inclined relative to the vertical direction v. The path F is a straight line inclined relative to the vertical direction v, the line connecting a middle point in the detecting surface of the FPD 4 in its initial position and that in its terminal position.

Figure 9:
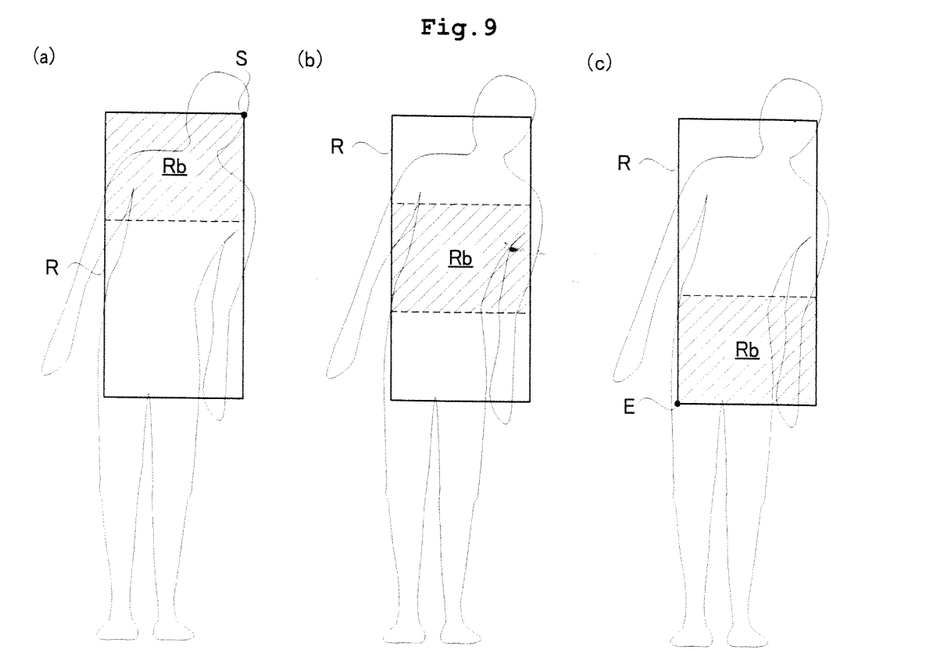
FIG. 9 is a schematic view showing an irradiation region of an X-ray beam during bending radiography according to the example of this invention.

In each radiography, X-rays are applied for each one time. Description will be given of the X-ray irradiation region in each radiography. X-rays are applied for three X-ray radiography while the irradiation region is moved in the vertical direction v. Specifically, a rectangular region Rb in FIG. 9(a) indicates an X-ray irradiation region for the first X-ray radiography. Here, one upper end of the region Rb in the vertical direction conforms to the starting point S. A rectangular region Rb in FIG. 9(b) indicates an X-ray irradiation region for the second X-ray radiography. Here, the region Rb is located at the center of the imaging region of object R in the vertical direction v. A rectangular region Rb in FIG. 9(c) indicates an X-ray irradiation region for the third X-ray radiography. Here, one lower end of the region Rb in the vertical direction conforms to the terminal point E. In any radiography, the width of the region Rb in the horizontal direction s conforms to the width of the imaging region of object R in the same direction. The positions of the region Rb in the first and the second radiography partially overlap to each other in the vertical direction v, whereas those in the second and third radiography partially overlap in the vertical direction v. Moreover, in any radiography, the X-ray tube 3 has the same focus for X-ray irradiation.

Description will be given of the detecting surface 4a and divergence of the X-ray beam. As is apparent from FIG. 8(c), the horizontal width of the imaging region of object R conforms to a sum of a horizontal width s1 of the detecting surface 4a and a moving width s2 by which the detecting surface 4a is moved in the horizontal direction s during successive taking of fluoroscopic X-ray images. Moreover, as is apparent from FIG. 9, divergence of the X-ray beam in the horizontal direction s conforms to the width of the imaging region of object R in the horizontal direction s. Consequently, the sum of the width S1 and the moving width S2 corresponds to the width of the cone-shaped X-ray beam in the horizontal direction s in the plane where the detecting surface 4a lies.

Figure 10:
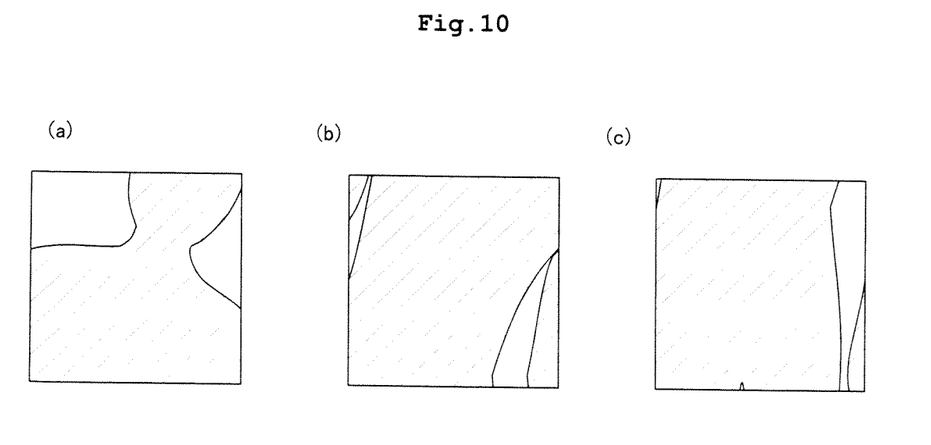
FIG. 10 is a schematic view showing fluoroscopic X-ray images for three-time bending radiography according to the example of this invention.

The FPD 4 detects X-rays transmitting through the subject M for every radiography, and sends out detection data to an image generating section 21. For instance, in the fluoroscopic X-ray images obtained in such way, the head and breast of the subject M is contained for the first radiography as in FIG. 10(a), the abdomen of the subject M is contained for the second radiography as in FIG. 10(b), and the waist of the subject M is contained for the third radiography as in FIG. 10(c). The fluoroscopic X-ray images are each sent out to a connecting section 22.

Figure 11:
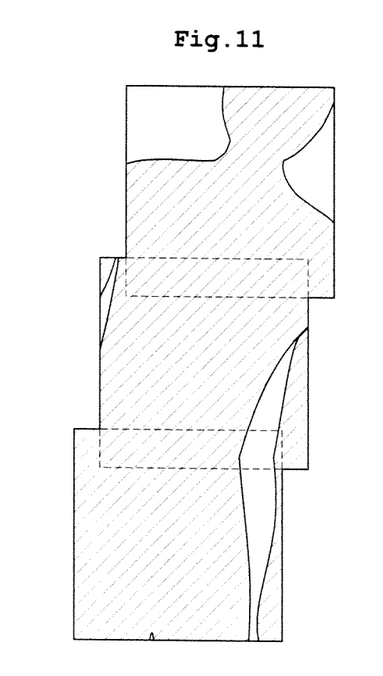
FIG. 11 is a schematic view of the connected fluoroscopic X-ray images according to the example of this invention.

The connecting section 22 superimposes the overlap portions of each fluoroscopic X-ray image to connect each fluoroscopic X-ray image, thereby generating a single image as shown in FIG. 11. Specifically, the position/opening calculating section 20 calculates positional information of each fluoroscopic X-ray image, and the image generating section 21 sends out the information in connection with each fluoroscopic X-ray image to the connecting section 22. Then the connecting section 22 superimposes each of the fluoroscopic X-ray images based on this. Alternatively, the connecting section 22 extracts the same portions of each of the fluoroscopic X-ray images by image analysis, and connects each of the fluoroscopic X-ray images so as to overlap the same portions. Here, the connecting section 22 operates similarly in the erect radiography step S1. The connected single fluoroscopic X-ray image is displayed on the display unit 26, and an inspection is completed.

As above, according to Example 1, two or more fluoroscopic X-ray images successively taken are connected to generate a single fluoroscopic X-ray image. Consequently, the fluoroscopic X-ray image for the subject M can be obtained although the detecting surface 4a of the FPD 4 fails to cover the imaging region of object R at once radiography. On the other hand, with the conventional configuration, when the subject M bending in the body-side direction is imaged for examinations of scoliosis, the subject M extends off the detecting surface 4a of the FPD 4 in the horizontal direction s. As a result, it is difficult to take the entire image of the subject M. Thus, according to Example 1, the detecting surface 4a is moved along the path F inclined relative to the vertical direction v to successively take fluoroscopic X-ray images of the subject M. Then the fluoroscopic X-ray images can be successively taken along bending curvature of the subject M, which enables to take an entire image of the bending subject M easily.

Specifically, the path F where the detecting surface 4a is moved is determined through identifying two vertices as the starting point S and the terminal point E on the diagonal of the rectangular imaging region of object R by the operator. Accordingly, the detecting surface 4a of the FPD 4 is moved as the way the operator instructs. Therefore, an X-ray apparatus capable of conducting examinations more easily can be provided.

Specifically, the width in the horizontal direction s of the cone-shaped X-ray beam in the plane where the detecting surface 4a of the FPD 4 lies conforms to a sum of the width in the horizontal direction s of the detecting surface 4a and the moving width by which the detecting surface 4a is moved in the horizontal direction s during successive imaging for fluoroscopic X-ray images. That is, the width in the horizontal direction s of the X-ray beam reliably covers the movable detecting surface 4a entirely. Such configuration can achieve successive imaging for fluoroscopic X-ray images without moving the X-ray tube 3 in the horizontal direction s. In other words, successive imaging is conducted while the focus for emitting X-rays from the X-ray tube 3is not moved. Consequently, images of the subject M appearing in each fluoroscopic X-ray image are taken with a common irradiation focus. Each fluoroscopic X-ray image is taken with common distortion. When they are connected to one another, no difference in level occurs in the connecting portions, which can achieve ideal connection of the images.

EXAMPLE 2

Description will be given next of Example 2. Example 2 has the same whole configuration as that of Example 1, and thus description thereof is to be omitted. Example 2 has a unique feature that an X-ray tube 3 is moved in a horizontal direction s during three-time radiography. On the other hand, the X-ray tube 3 is not moved in a vertical direction v during X-ray radiography.

Figure 12:
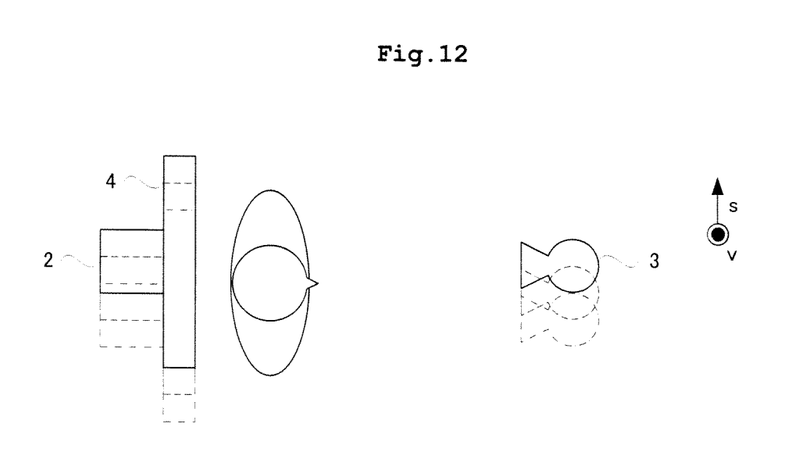
FIG. 12 is a schematic view showing movement of an X-ray tube for bending radiography according to another example of this invention.

Detailed description will be given of movement of the X-ray tube 3 according to Example 2. FIG. 12 is a conceptual view showing radiography to a subject M seen downward in the vertical direction v. A position of each element 2, 3, 4 in the first radiography is indicated by solid lines in FIG. 12, whereas a position of each element 2, 3, 4, in the second radiography is indicated by dotted lines in FIG. 12. In addition, a position of each element 2, 3, 4 in the third radiography is indicated by dashed lines in FIG. 12. Such configuration of Example 2 can achieve movement of the X-ray tube 3 in the horizontal direction s along with movement of the FPD 4. Specifically, the X-ray tube 3 is moved in the horizontal direction s as the strut 2 is moved such that a relative relationship between the X-ray tube 3 and the FPD 4 can be constant in the horizontal direction s.

Figure 13:
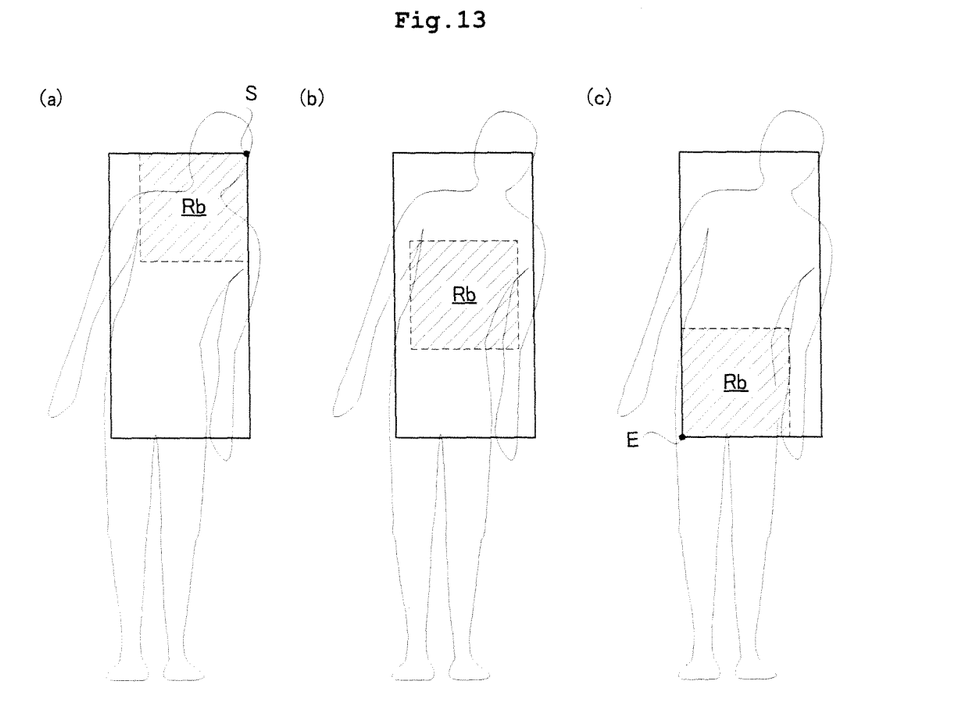
FIG. 13 is a schematic view showing an irradiation region of an X-ray beam during bending radiography according to the other example of this invention.

Description will be given next of X-ray irradiation region upon three-time bending radiography according to Example 2. Specifically, X-rays are emitted upon three-time X-ray radiography while the X-ray irradiation region is moved in the vertical direction v. Specifically, as shown in FIGS. 13(a) to 13(c), a rectangular region R2 in each X-ray radiography where X-rays are applied conforms to a position of the detecting surface 4a shown in FIG. 8. The positions of the region R2 in the first and the second X-ray radiography partially overlap to each other in the vertical direction v, whereas those in the second and third X-ray radiography partially overlap in the vertical direction v.

As mentioned above, according to Example 2, the fluoroscopic X-ray images can be successively taken while the X-ray tube 3 is moved in the horizontal direction s along with movement of the strut 2 in the horizontal direction s.

Description will be given of the detecting surface 4a and divergence of the X-ray beam. As shown in FIGS. 13 and 8, the region R2 conforms to the detecting surface 4a. Accordingly, the cone-shaped X-ray beam on the plane where the detecting surface 4a lies has the same width in the horizontal direction s as that of the detecting surface 4a.

As noted above, according to Example 2, successive imaging is conducted while the X-ray tube 3 moves the focus for emitting X-rays in the horizontal direction s. Such configuration can achieve the constant relative relationship between the X-ray tube 3 and the FPD 4 in the horizontal direction s. Consequently, the center axis of the X-ray beam can be located at the center of the detecting surface 4a of the FPD 4 in every radiography. As a result, fluoroscopic X-ray images having the center with less distortion can be obtained.

Moreover, in Example 2, successive imaging is conducted while the X-ray tube 3 moves the focus for emitting X-rays in the horizontal direction s. When the cone-shaped X-ray beam on the plane where the detecting surface 4a of FPD 4 lies has the same width in the horizontal direction s as that of the detecting surface 4a, the X-ray beam can be applied to the subject M without extending off the detecting surface 4a in the horizontal direction s. Consequently, the X-ray apparatus can be provided that can minimize an exposure to the subject.

Figure 14:
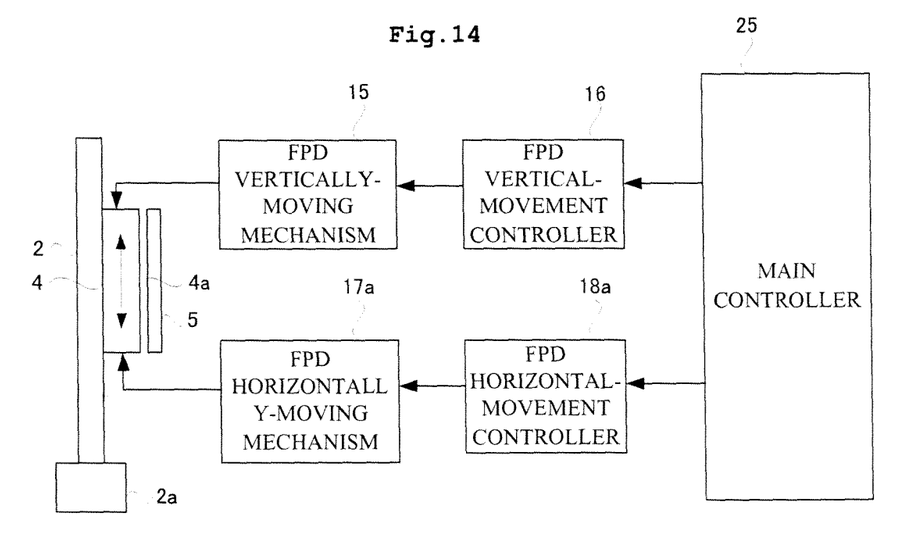
FIG. 14 is a functional block diagram showing one modification of this invention.

This invention is not limited to each example, but may be modified as follows:

(1) In each example, the FPD 4 is moved horizontally through horizontal movement of the strut 2 for supporting the FPD 4. Alternatively, the FPD 4 may be moved horizontally through parallel movement thereof relative to the strut 2. According to this modification, it is not necessary for the strut 2 to be moved horizontally. As a result, the strut moving mechanism 17 and the strut movement controller 18 in FIG. 1 are not needed. This modification shown in FIG. 14 includes, in addition to the FPD vertically-moving mechanism 15 and the FPD vertical-movement controller 16, an FPD horizontally-moving mechanism 17a for modifying a position of the FPD 4 relative to the strut 2 into the horizontal direction and an FPD horizontal-movement controller 18a for controlling this.

(2) Each foregoing example discusses a medical apparatus. This invention is also applicable to apparatus for industrial use and for the nuclear field.

(3) The X-rays in each foregoing examples are one example of radiation in this invention. Therefore, this invention may be adapted also for radiation other than X-rays.

(4) Each foregoing example includes no top board. This invention is not limited to this configuration. This application is applicable to a radiographic apparatus with a top board that images a subject M lying on the back thereof on the top board.

INDUSTRIAL UTILITY

This invention is suitable for a radiographic apparatus for medical uses.

DESCRIPTION OF REFERENCES

F . . . path
2 . . . strut
3 . . . X-ray tube (radiation source)
4 . . . FPD (radiation detecting device)
4a . . . detecting surface
15 . . . FPD vertically-moving mechanism (detector vertically-moving device)
16 . . . FPD vertical-movement controller (detector vertical-movement control device)
17 . . . strut moving mechanism (strut moving device)
18 strut movement controller (strut movement control device)
21 . . . image generating section (image generating device)
22 . . . connecting section (connecting device)
27 . . . console (input unit)

The invention claimed is:

1. A radiographic apparatus comprising:
a radiation source for emitting radiation;
a radiation detecting device having a detecting surface for detecting the radiation;
a strut extending in a vertical direction for supporting the radiation detecting device;
(A1) a strut moving device for moving the strut in a horizontal direction that is orthogonal to a direction from the radiation source toward the radiation detecting device;
(B1) a strut-movement control device for controlling the strut moving device;
a detector vertically-moving device for moving the radiation detecting device vertically relative to the strut;
a detector vertical-movement control device for controlling the detector vertically-moving device;
an image generating device for successively generating images of a subject based on detection data outputted from the radiation detecting device;
a connecting device for connecting two or more images successively taken to generate a single image; and
an input unit for inputting an operator's instruction of a moving path for the radiation detecting device, the moving path extending in a direction different from the vertical and horizontal directions,
the detecting surface being placed along a plane formed by the vertical and horizontal directions,
the strut-movement control device and the detector vertical-movement control device being configured to control the strut moving device and the detector vertically-moving device to move the radiation detecting device along the moving path for successively taking the images of the subject.

2. The radiographic apparatus according to claim 1, further comprising:
the path where the detecting surface is moved during successive imaging is set by the operator through identifying two vertices on a diagonal of the rectangular imaging region.

3. The radiographic apparatus according to claim 1, further comprising:
a collimator for collimating the radiation emitted from the radiation source into a cone-shaped radiation beam, wherein
the cone-shaped radiation beam in a plane where the detecting surface of the radiation detecting device lies has a horizontal width corresponding to a sum of a horizontal width of the detecting surface and a moving width by which the detecting surface is moved in the horizontal direction during successive imaging.

4. The radiographic apparatus according to claim 1, further comprising:
a radiation-source moving device for moving the radiation source in the horizontal direction viewed from the radiation detecting device; and
a radiation-source movement control device for controlling the radiation-source moving device, wherein
the radiation source being moved horizontally along with horizontal movement of the strut such that a relative relationship in the horizontal direction between the radiation source and the radiation detecting device is constant, whereby the images are successively taken.

5. The radiographic apparatus according to claim 4, further comprising:
a collimator for collimating the radiation emitted from the radiation source into a cone-shaped radiation beam, wherein
the cone-shaped radiation beam in a plane where the detecting surface of the radiation detecting device lies has a horizontal width corresponding to a horizontal width of the detecting surface.

6. A radiographic apparatus comprising:
a radiation source for emitting radiation;
a radiation detecting device having a detecting surface for detecting the radiation;
a strut extending in a vertical direction for supporting the radiation detecting device;
(A2) a detector horizontally-moving device for moving the radiation detecting device relative to the strut in a horizontal direction that is orthogonal to a direction from the radiation source toward the radiation detecting device;
(B2) a detector horizontal-movement control device for controlling the detector horizontally-moving device;
a detector vertically-moving device for moving the radiation detecting device vertically relative to the strut;
a detector vertical-movement control device for controlling the detector vertically-moving device;
an image generating device for successively generating images of a subject based on detection data outputted from the radiation detecting device;
a connecting device for connecting two or more images successively taken to generate a single image; and
an input unit for inputting an operator's instruction of a moving path for the radiation detecting device, the moving path extending in a direction different from the vertical and horizontal directions,
the detecting surface being placed along a plane formed by the vertical and horizontal directions,
the detector horizontal-movement control device and the detector vertical-movement control device being configured to control the detector horizontally-moving device and the detector vertically-moving device to move the radiation detecting device along the moving path for successively taking the images of the subject.

* * * * *